United States Patent [19]

Boase et al.

[11] Patent Number: 4,632,936
[45] Date of Patent: Dec. 30, 1986

[54] INSECTICIDAL COMPOSITIONS

[75] Inventors: Clive J. Boase, Sawston; Howard B. Dawson, St. Ives, both of England

[73] Assignee: FBC Limited, England

[21] Appl. No.: 743,269

[22] Filed: Jun. 10, 1985

Related U.S. Application Data

[63] Continuation of Ser. No. 571,606, Jan. 17, 1984, abandoned.

[30] Foreign Application Priority Data

Jan. 22, 1983 [GB] United Kingdom ............... 8301794

[51] Int. Cl.$^4$ .................. A01N 43/30; A01N 47/10; A01N 25/00
[52] U.S. Cl. ................................. 514/465; 514/490; 514/770
[58] Field of Search ............... 514/465, 490, 770

[56] References Cited

U.S. PATENT DOCUMENTS

| | | |
|---|---|---|
| 3,232,831 | 2/1966 | Schwint ........................... 514/770 |
| 4,134,977 | 1/1979 | Greenberg ....................... 424/225 |
| 4,189,475 | 2/1980 | Hennart .......................... 424/282 |
| 4,191,764 | 3/1980 | Beard ............................... 514/374 |
| 4,226,883 | 10/1980 | Yamamoto et al. ............. 424/300 |
| 4,305,953 | 12/1981 | Pfliegel et al. .................. 514/388 |
| 4,495,228 | 1/1985 | Cornwell ........................ 427/385.5 |

OTHER PUBLICATIONS

The Merck Index; 9th edition (1976); #1041, #7625.
Chemical Abstracts; vol. 24 (1930); Zacher et al., "Investigations on the Insecticidal Actions of Oxides and Carbonates".
Filed in Parent Application Ser. No. 06/571,606.

*Primary Examiner*—Leonard Schenkman
*Assistant Examiner*—Joseph A. Lipovsky
*Attorney, Agent, or Firm*—Ostrolenk, Faber, Gerb & Soffen

[57] ABSTRACT

The persistance of bendiocarb and propoxur deposited on both porous and non-porous surfaces is increased by the addition of silica to formulations, in which the insecticides are dissolved in organic solvent.

2 Claims, No Drawings

INSECTICIDAL COMPOSITIONS

This is a continuation of Ser. No. 571,606, filed 1/17/84, now abandoned.

This invention relates to pesticidal compositions and in particular to compositions containing the carbamate insecticides, 2,2-dimethyl-1,3-benzodioxol-4-yl methylcarbamate and 2-(1-methylethoxy)phenyl methylcarbamate, hereafter referred to by their common names, bendiocarb and propoxur respectively.

It is known that silica can be added to insecticides to improve their performance. Thus in G.B. Pat. No. 1 267 974 silica is added to carbaryl to improve its action against insects on animal hair. The formulations disclosed in this patent however are all powder formulations.

When bendiocarb is applied from solution to a porous surface, the surface absorbs active material and persistence is reduced. We have found that the persistence of bendiocarb can be improved by addition of silica. Surprisingly the silica also improves the persistence and hence performance of bendiocarb on non-porous surfaces. Silica similarly improves the performance of propoxur.

Thus according to the invention, there is provided an insecticidal composition which comprises a solution of a carbamate insecticide selected from bendiocarb and propoxur in one or more organic solvents, in admixture with finely divided silica.

The insecticide is usually present in an amount of 0.1 to 5%, e.g. 0.2 to 1% w/v. The silica is usually present in and an amount of 0.1 to 5%, e.g. 0.5 to 2% w/v, and is generally of small particle size of 5 to 50 nanometers. It is preferably pyrogenic silica, e.g. that obtained by high temperature pyrolysis of a suitable silicon compound.

It is generally desirable to include at least two solvents. One of these is preferably a chlorinated hydrocarbon, e.g. dichloromethane and the other is preferably a hydrocarbon or a mixture of hydrocarbons. If desired, the formulation can be in the form of an aerosol containing for example from 20 to 60% by volume of propellant (with consequent reduction in the amount of the other ingredients). Any conventional propellant may be used, e.g. propane and/or butane, carbon dioxide or one or more chlorofluorohydrocarbons, such as chlorodifluoromethane, dichlorofluoromethane or 1,1,2-trichloro-1,2,2-trifluoroethane. In addition the formulation may include a "knock-down" agent such as tetramethrin or dichlorvos.

The invention is illustrated in the following Examples.

EXAMPLE 1

A ready-for-use preparation was formulated as follows:

|  | % |
| --- | --- |
| Bendiocarb | 0.4 w/v |
| dichloromethane | 25 v/v |
| pyrogenic silica ("Aerosil 200") | 1 w/v |
| kerosene | to 100 by volume |

For the purposes of comparison, a similar preparation was formulated in which the silica was omitted.

0.4 ml of each formulation was pipetted onto 10×10 cm tiles of plastic laminate and of plywood (representing a non-porous and a porous surface, respectively). The liquid was spread with a microscope slide to give an even film and four replicates of each formulation on each surface were prepared. At intervals batches of 10 adult male cockroaches (*Blatella germanica*) were confined in a 9.5 cm diameter glass ring coated with polytetrafluoroethylene on each tile. Mortality was noted at various intervals.

The 24-hour % mortalities recorded were as follows:

|  | Formulation | | | | | | | |
| --- | --- | --- | --- | --- | --- | --- | --- | --- |
|  | Plastic Age of deposit in days | | | | Plywood Age of deposit in days | | | |
|  | 1 | 8 | 15 | 28 | 1 | 8 | 15 | 28 |
| Invention | 100 | 100 | 100 | 33 | 100 | 100 | 100 | 97 |
| Comparison | 100 | 100 | 7.5 | 0 | 100 | 100 | 86 | 5 |

It will be seen that addition of the silica results in an increase in the active life of the insecticide deposit both on porous and non-porous surfaces.

EXAMPLE 2

The plastic laminate test of Example 1 was repeated with similar formulations in which the bendiocarb was replaced by propoxur. % mortalities recorded after 1 hour exposure to the treated laminate was as follows:

|  | Formulation | | |
| --- | --- | --- | --- |
|  | Age of Deposit in days | | |
|  | 1 | 7 | 14 |
| Invention | 100 | 100 | 65 |
| Comparison | 100 | 0 | 0 |

As in Example 1 the addition of silica results in an increase in the active life of the insecticide.

We claim:

1. An insecticidal composition which comprises a solution of a carbamate insecticide selected from the group consisting of bendiocarb and propoxur in one or more organic solvents in admixture with finely divided pyrogenic silica having a particle size of 5 to 50 nanometers, and wherein the insecticide is present in an amount of 0.2 to 1% w/v and the silica is present in an amount of 0.5 to 2% w/v.

2. A composition according to claim 1 in which the solvent comprises a chlorinated hydrocarbon.

* * * * *